United States Patent
Xu et al.

(10) Patent No.: US 10,058,698 B2
(45) Date of Patent: Aug. 28, 2018

(54) ASYMMETRIC COCHLEAR IMPLANT ELECTRODES AND METHOD

(71) Applicant: Advanced Bionics AG, Staefa (CH)

(72) Inventors: Bing Xu, Valencia, CA (US); Kurt J. Koester, Los Angeles, CA (US); Mark B. Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/911,690

(22) PCT Filed: Aug. 27, 2013

(86) PCT No.: PCT/US2013/056900
§ 371 (c)(1),
(2) Date: Feb. 11, 2016

(87) PCT Pub. No.: WO2015/030738
PCT Pub. Date: Mar. 5, 2015

(65) Prior Publication Data
US 2016/0199637 A1 Jul. 14, 2016

(51) Int. Cl.
*A61N 1/05* (2006.01)
*A61N 1/36* (2006.01)

(52) U.S. Cl.
CPC ....... *A61N 1/0541* (2013.01); *A61N 1/36036* (2017.08)

(58) Field of Classification Search
CPC .................................................. A61N 1/0541
See application file for complete search history.

(56) References Cited

U.S. PATENT DOCUMENTS

| | | | |
|---|---|---|---|
| 3,752,939 A | 8/1973 | Bartz | |
| 4,261,372 A | 4/1981 | Hansen | |
| 4,284,085 A | 8/1981 | Hansen | |
| 4,502,492 A | 3/1985 | Bornzin | |
| 4,762,135 A | 8/1988 | Van Der Puije | |
| 4,827,932 A | 5/1989 | Ideker | |
| 4,938,231 A | 7/1990 | Milijasevic | |
| 5,042,463 A | 8/1991 | Lekholm | |
| 5,344,387 A | 9/1994 | Lupin | |

(Continued)

FOREIGN PATENT DOCUMENTS

| | | |
|---|---|---|
| EP | 2286871 A2 | 2/2011 |
| EP | 2298408 A2 | 3/2011 |

(Continued)

OTHER PUBLICATIONS

Ruddy, et al. "Influence of materials and geometry on fields produced by cochlear electrode arrays", Medical & Biological Engineering & Computing, 1995, 793-801, 33.

(Continued)

*Primary Examiner* — George Evanisko
(74) *Attorney, Agent, or Firm* — Fabian Vancott; Steven L. Nichols (57) ABSTRACT

An implantable lead may include an insulating substrate and a first asymmetric electrode formed on the insulating substrate. The first asymmetric electrode may have external perimeter edges defining a boundary between an exposed portion of the first electrode and the insulating substrate, wherein the external perimeter edges of the first electrode have asymmetric edge lengths.

20 Claims, 6 Drawing Sheets

(56) References Cited

U.S. PATENT DOCUMENTS

| | | | |
|---|---|---|---|
| 5,454,370 A | 10/1995 | Avitall | |
| 5,649,970 A | 7/1997 | Loeb | |
| 6,074,422 A | 6/2000 | Berrang | |
| 6,304,787 B1 * | 10/2001 | Kuzma | A61N 1/0541 607/115 |
| 6,309,410 B1 | 10/2001 | Kuzma | |
| 6,374,143 B1 * | 4/2002 | Berrang | A61N 1/0541 600/379 |
| 6,546,292 B1 | 4/2003 | Steinhaus | |
| 6,779,257 B2 | 8/2004 | Kiepen | |
| 6,889,094 B1 | 5/2005 | Kuzma | |
| 7,326,649 B2 | 2/2008 | Rodger | |
| 7,706,888 B2 | 4/2010 | Jolly | |
| 7,983,768 B2 | 7/2011 | Dadd | |
| 8,000,798 B2 | 8/2011 | Gantz | |
| 8,014,878 B2 | 9/2011 | Greenberg | |
| 8,126,564 B2 | 2/2012 | Gantz | |
| 8,180,460 B2 | 5/2012 | Neysmith | |
| 8,190,271 B2 | 5/2012 | Overstreet | |
| 8,250,745 B1 | 8/2012 | Orinski | |
| 8,332,052 B1 | 12/2012 | Orinski | |
| 8,880,193 B1 | 11/2014 | Thenuwara | |
| 9,056,196 B2 | 6/2015 | Thenuwara | |
| 9,211,403 B2 | 12/2015 | Tortonese | |
| 2002/0019669 A1 | 2/2002 | Berrang | |
| 2005/0038489 A1 * | 2/2005 | Grill | A61N 1/05 607/116 |
| 2005/0256561 A1 | 11/2005 | Gantz | |
| 2006/0074460 A1 | 4/2006 | Maghribi | |
| 2006/0116743 A1 | 6/2006 | Gibson | |
| 2006/0247754 A1 | 11/2006 | Greenberg | |
| 2006/0259112 A1 | 11/2006 | Greenberg | |
| 2007/0112402 A1 * | 5/2007 | Grill | A61N 1/375 607/115 |
| 2007/0179566 A1 | 8/2007 | Gantz | |
| 2007/0203557 A1 | 8/2007 | Gantz | |
| 2007/0251082 A1 | 11/2007 | Milojevic | |
| 2007/0293749 A1 | 12/2007 | Zhou | |
| 2008/0015669 A1 * | 1/2008 | Jolly | A61N 1/0541 607/116 |
| 2008/0019518 A1 | 1/2008 | Mito | |
| 2008/0057179 A1 | 3/2008 | Greenberg | |
| 2008/0064946 A1 | 3/2008 | Greenberg | |
| 2008/0195178 A1 | 8/2008 | Kuzma | |
| 2008/0234793 A1 | 9/2008 | Gibson | |
| 2008/0288036 A1 | 11/2008 | Greenberg | |
| 2008/0288037 A1 * | 11/2008 | Neysmith | A61N 1/0543 607/116 |
| 2008/0312717 A1 | 12/2008 | Gantz | |
| 2009/0030483 A1 | 1/2009 | Risi | |
| 2009/0143848 A1 | 6/2009 | Greenberg | |
| 2009/0306745 A1 * | 12/2009 | Parker | A61N 1/0541 607/57 |
| 2010/0106134 A1 | 4/2010 | Jolly | |
| 2010/0168830 A1 | 7/2010 | Hung | |
| 2010/0204768 A1 | 8/2010 | Jolly | |
| 2011/0202120 A1 | 8/2011 | Ball | |
| 2011/0264168 A1 | 10/2011 | Dadd | |
| 2011/0301665 A1 | 12/2011 | Mercanzini | |
| 2011/0319907 A1 | 12/2011 | Gallegos | |
| 2012/0004715 A1 | 1/2012 | Ramachandran | |
| 2012/0158113 A1 * | 6/2012 | Jolly | A61N 1/0541 607/137 |
| 2012/0192416 A1 | 8/2012 | Neysmith | |
| 2014/0303703 A1 | 10/2014 | Mercanzini | |
| 2014/0336739 A1 | 11/2014 | Lotfi | |
| 2015/0267314 A1 | 9/2015 | Thenuwara | |
| 2015/0320550 A1 | 11/2015 | Downing | |

FOREIGN PATENT DOCUMENTS

| | | |
|---|---|---|
| WO | 0112115 | 2/2001 |
| WO | 2008011721 A9 | 1/2008 |
| WO | 2009062114 A2 | 5/2009 |
| WO | 2009121110 | 10/2009 |
| WO | 2010055421 | 5/2010 |
| WO | 2011075480 | 6/2011 |
| WO | 2012003295 A1 | 1/2012 |
| WO | 2012003297 A1 | 1/2012 |
| WO | 2012034162 A2 | 3/2012 |
| WO | 2012154256 | 11/2012 |
| WO | 20140105059 A1 | 12/2012 |
| WO | 2013048396 A1 | 4/2013 |
| WO | 2013103489 | 7/2013 |
| WO | 2015023280 | 2/2015 |
| WO | 2015030734 A | 3/2015 |

OTHER PUBLICATIONS

Wei, et al.; "Analysis of high-perimeter planar electrodes for efficient neural stimulation"; Frontiers in Neuroengineering; Nov. 2009; vol. 2.

Wei, Xuefeng Frank; "Analysis and Design of Electrodes for Deep Brain Stimulation"; Doctoral Thesis; Dept. of Biomedical Engineering; Duke University; 2009.

* cited by examiner

ASYMMETRIC COCHLEAR IMPLANT ELECTRODES AND METHOD

BACKGROUND

Neurostimulating devices stimulate nerves by applying an electrical current. Such devices often include a biocompatible implantable lead that carries current from a pulse generator or Radio Frequency (RF) link to the stimulation site. One or more electrodes on the implantable lead interface with the biological tissue at the stimulation site. The electrical impedance of the implantable lead is related to a number of parameters, including the impedance of the interface of the electrodes with the biological tissue. Reducing the impedance of the implantable lead can be desirable for a number of reasons, including more efficient delivery of electrical stimulation and longer battery life.

BRIEF DESCRIPTION OF THE DRAWINGS

The accompanying drawings illustrate various examples of the principles described herein and are a part of the specification. The illustrated examples are merely examples and do not limit the scope of the claims.

Throughout the drawings, identical reference numbers designate similar, but not necessarily identical, elements.

DETAILED DESCRIPTION

Neurostimulating devices find wide spread use to compensate for deficient or malfunctioning biological structures or systems. For example, a neurostimulating device can be effectively used to improve the performance of impaired auditory, visual, and central nervous systems. These neurostimulating devices include an implantable lead that includes a number of electrodes and wires connected to those electrodes. The implantable lead allows the electrodes to be placed in proximity to the desired nerves. A current source is typically placed in a more accessible area that is away from the nerves. The current source is connected to the electrodes by the wires in the implantable lead. The electrical impedance of the implantable lead is related to a number of parameters, including the impedance of the interface of the electrodes with the biological tissue. Reducing the impedance of the interface between the electrodes and the biological tissue can be desirable for a number of reasons, including more efficient delivery of electrical stimulation and longer battery life. It can also be desirable to focus the electrical stimulation on target tissue while minimizing the field in non-target tissue.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with the example is included in at least that example, but not necessarily in other examples. Features shown and/or described in connection with one figure may be combined with features shown and/or described in connection with other figures.

Figure 1:
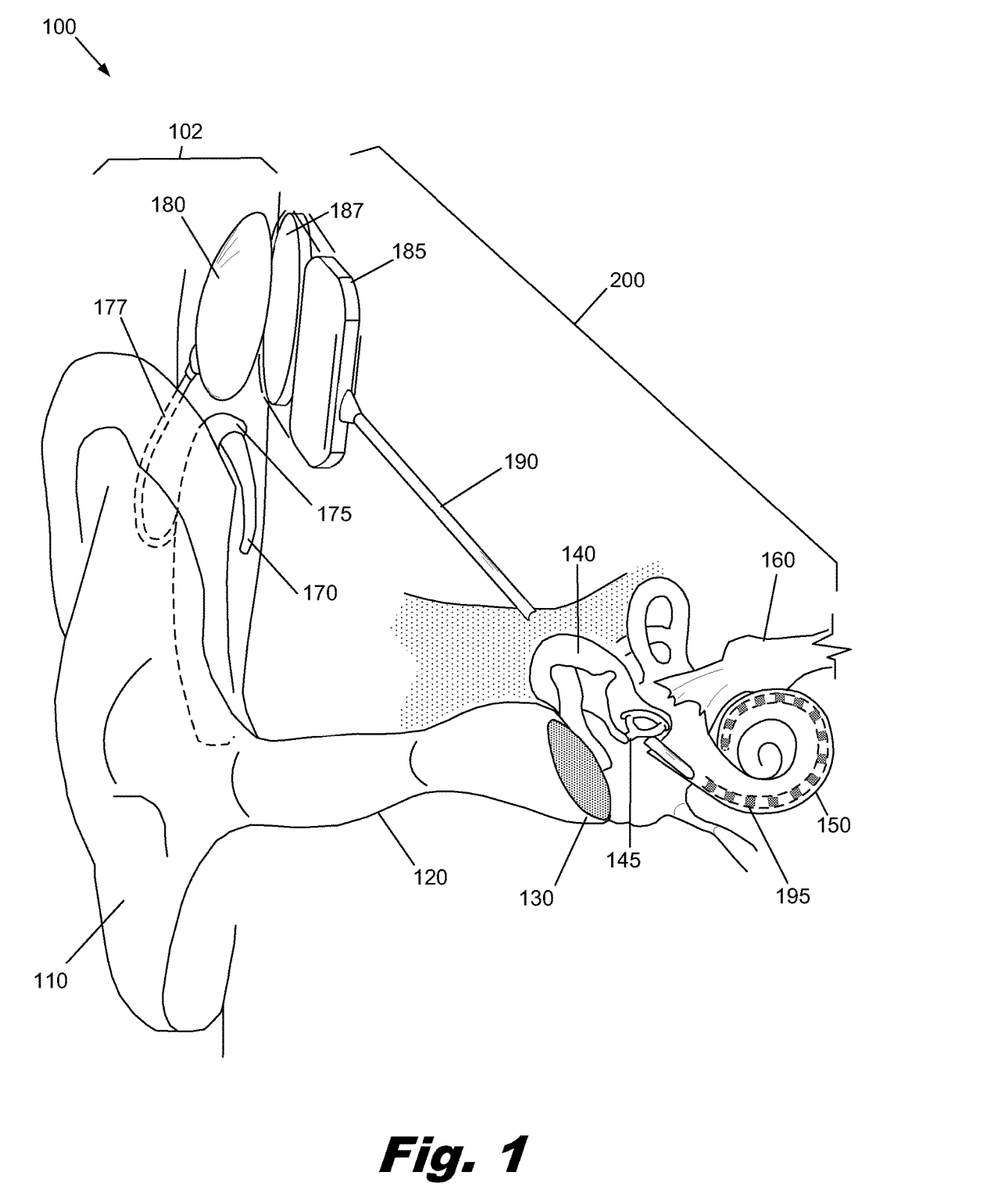
FIG. 1 shows a cochlear implant system in use by a patient, according to one example of principles described herein.

FIG. 1 is a diagram showing one illustrative example of a neurostimulating cochlear implant system (100) that includes an internal implanted portion (200) and an external portion (102). In a functioning human ear, sound enters the external ear (110) and passes through the ear canal (120) to the ear drum (130). A series of three small bones (145) in the middle ear (140) amplify the motion of the ear drum and transmit the amplified signals to the cochlea (150). Fluid inside the cochlea moves in response to the amplified signals. Hair cells in the cochlea convert the motion of the fluid into nerve impulses that travel through the auditory nerve (160) to the brain.

The cochlear implant system (100) provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Figures 2A, 2B:
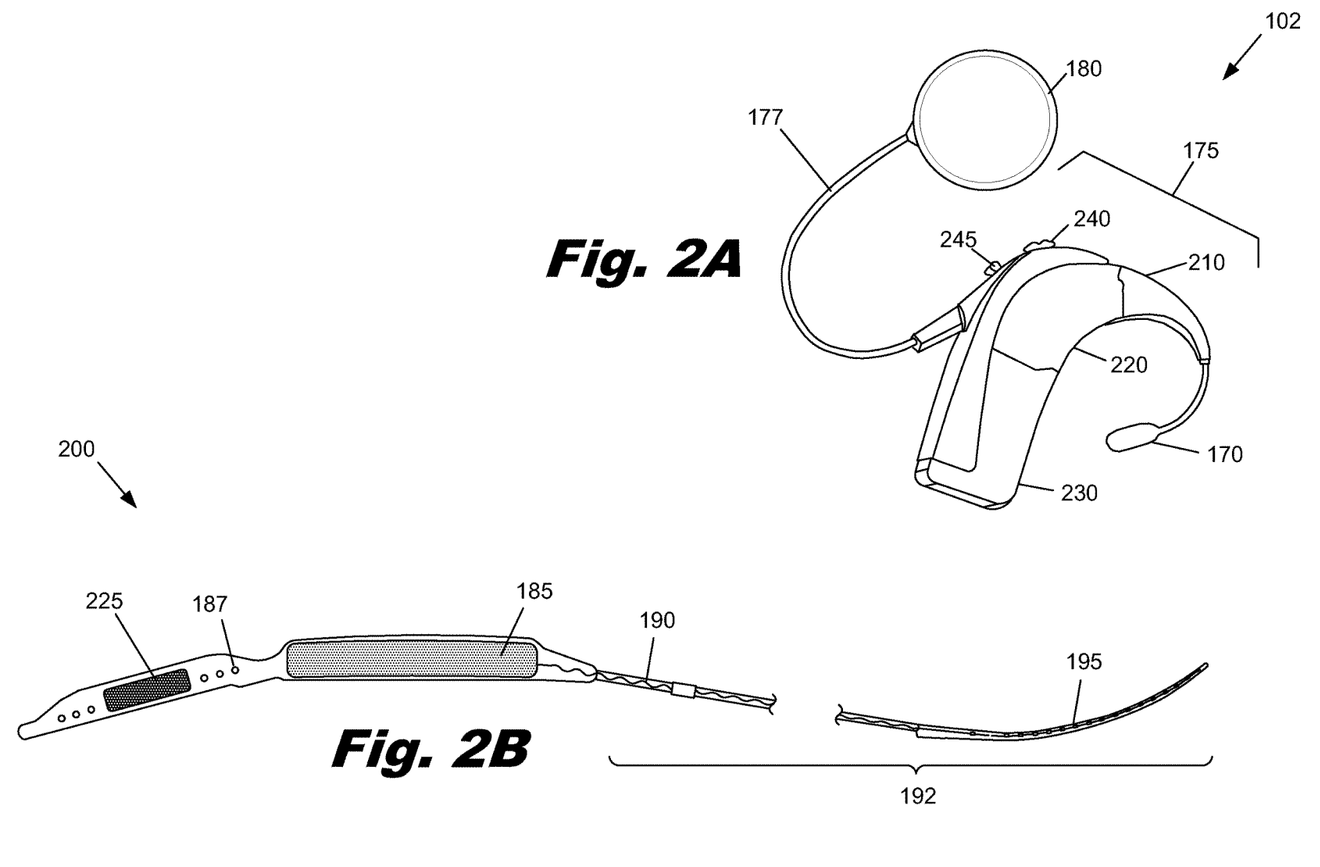
FIGS. 2A and 2B show the external and internal portions of a cochlear implant system, respectively, according to one example of principles described herein.

The external portion (102) of the cochlear implant system (100) can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the BTE unit (175) and transmits them to the implanted antenna assembly (187) by electromagnetic transmission. FIG. 2A shows the external portion (102) of the cochlear implant system, including the BTE unit (175), battery (230), processor (220), ear hook (210), and microphone (170). A number of controls (240, 245) are located on the processor (220). These controls may include an on/off switch (245) and volume switch (240). The cable (177) connects the processor (220) to the transmitter (180).

Now referring back to FIG. 1, the internal implanted portion (200) of the cochlear implant system includes an electrode array (195) that is surgically placed within the patient's cochlea (150). Unlike hearing aids, the cochlear implant system (100) does not amplify sound, but works by directly stimulating any functioning auditory nerve cells inside the cochlea (150) with electrical impulses representing the ambient acoustic sound. This bypasses the defective cochlear hair cells that normally transduce acoustic energy into electrical energy. The implanted portion (200) of the cochlear implant system is shown in FIG. 1 in its implanted configuration and in FIG. 2B before implantation. The implanted portion (200) of the cochlear implant (100) includes an internal processor (185), an antenna assembly (187), and an implantable lead (192). The implantable lead (192) includes a lead body (190) and an electrode array (195). The internal processor (185) and antenna assembly (187) are secured beneath the user's skin, typically above and behind the external ear (110). The antenna assembly (187) receives signals and power from the transmitter (180). The internal processor (185) receives these signals and operates on the signals to generate modified signals. These modified signals are then sent through the lead body (190) to the electrode array (195), which is at the distal portion of the implantable lead (192) and is implanted within the cochlea (150). The electrode array uses the modified signals to provide electrical stimulation to the auditory nerve (160).

FIG. 2B is a side view of the implanted portion (200) of a cochlear implant (100, FIG. 1). The implanted portion (200) includes the antenna assembly (187) and the processor (185). In this example, the antenna assembly (187) is external from the processor (185). A magnet (225) is disposed in the center of the antenna assembly (187). The magnet (225) removably secures the transmitter (180, FIG. 1) over the antenna assembly (187). The antenna assembly (187) is connected to the processor (185). The implantable lead (192) is connected to the opposite side of the processor (185). The implantable lead (192) includes the electrode array (195) and the lead body (190).

Figure 3A:
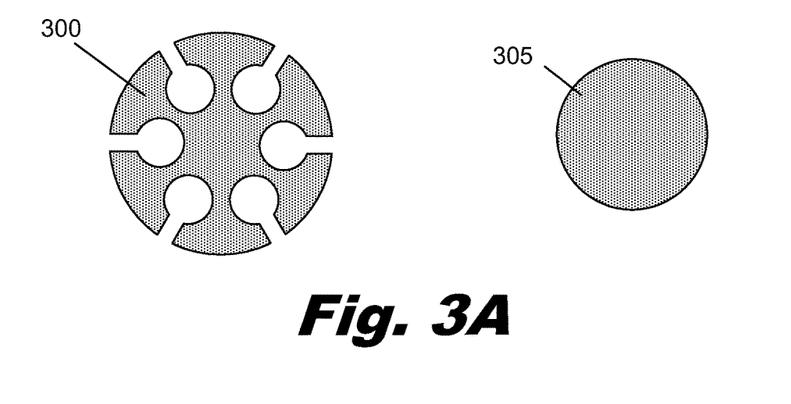
FIGS. 3A, 3B, and 3C show comparisons between long edge length electrodes and electrodes with the similar surfaces areas but shorter edge lengths, according to one example of principles described herein.
Figure 3B:
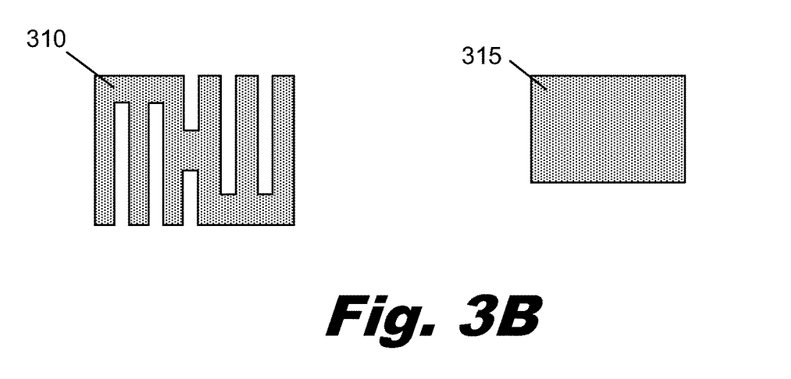
Figure 3C:
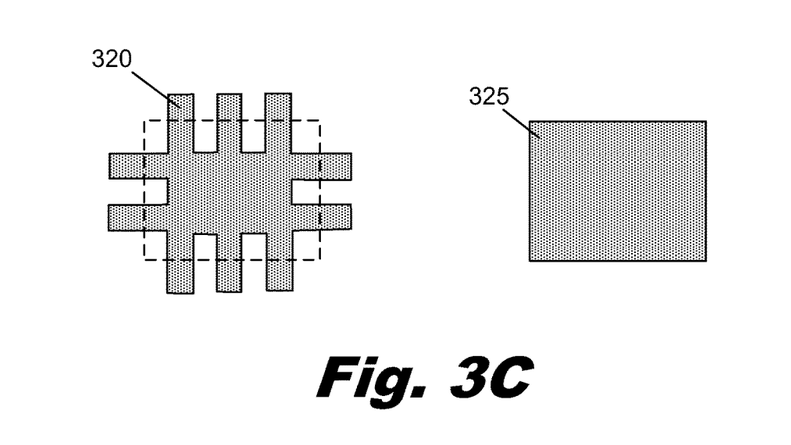

FIGS. 3A, 3B, and 3C show examples of electrodes with long edge lengths that could be used in a variety of implantable leads. For example, FIG. 3A shows two electrodes (300, 305) that have approximately the same surface area but different perimeter edge lengths. Current densities at the electrode/tissue interface are highest at the edges of the electrodes. Thus, the impedance of the electrode is not uniform over its area. The edges have lower impedance and the interior portions have higher impedance. The term impedance refers to the overall resistance to the flow of electrical current through a circuit. Impedance may have capacitive, inductive and resistance components. By increasing the edge length of an electrode, i.e., making the edge length longer, the electrical impedance decreases. In particular, an electrode with higher edge length-to-surface area ratio will have lower impedance than an electrode with the same surface area but lower edge length-to-surface area ratio. In FIG. 3A, the left electrode and the right electrode have approximately the same surface area, but the electrode on the left has a much longer edge length. This is accomplished by making a number of circular cutouts in the electrode interior and then connecting these circular cutouts to the outer perimeter with channels. This creates an electrode with a significantly longer edge length and lower electrical impedance. The electrode on the left can be more efficient in delivering electrical stimulation to surrounding biological tissue than the electrode on the right.

FIG. 3B shows another example of a pair of electrodes (310, 315) that have similar surface area but different edge lengths. In this example, the electrodes (310, 315) have a rectangular shape. The long edge length electrode (310) has a number of slots that extend from the perimeter into its interior. The slots significantly increase the edge length of the electrode. The electrode (315) on the right has approximately the same surface area but a much shorter edge length. Using an arbitrary unit length to measure both electrodes, the electrode on the right (315) has an edge length of approximately 14.4 units and a surface area of approximately 12.6 units square. This results in an edge length to surface area ratio of approximately 1:1. The electrode on the left (310) has an edge length of approximately 50 and approximately the same surface area as the electrode (315) on the right. This results in an edge length to surface area ratio of greater than 4:1.

FIG. 3C shows another example of a pair of electrodes (320, 325) that have similar surface area but different edge lengths. In this example the edge length to surface area of the electrode on the right (325) is slightly less than 1:1, meaning that the edge length in linear units is slightly less than the surface area in square units. The electrode on the left (320) has an edge length to surface area ratio that is greater than 2:1. Because of the longer edge lengths of the electrodes on the left (300, 310, 320), they will have lower impedance and more effectively pass electrical currents to the biological tissues than the electrodes on the right (305, 315, 325).

FIGS. 4A-4C and FIGS. 5A-5E show various examples of asymmetric electrodes (400, 410, 415, 500) formed on an insulating substrate. The asymmetric electrodes include external perimeter edges that have asymmetric edge lengths. In general, the external perimeter edges define a boundary between an exposed portion of the electrodes and the insulating substrate. These external perimeter edges include a smooth edge that has a short edge length and a patterned edge comprising a long edge length. A "patterned" edge has a varying profile that may be described as jagged, toothed, serpentine, uneven, regular, castellated, or irregular. In general, the patterned edge or edges of the electrode have a significantly longer length than the smooth edge or edges of the electrode. A smooth edge is generally linear or curved and takes a substantially shorter path between two points or corners of the electrode than the patterned edge.

Figure 4A:
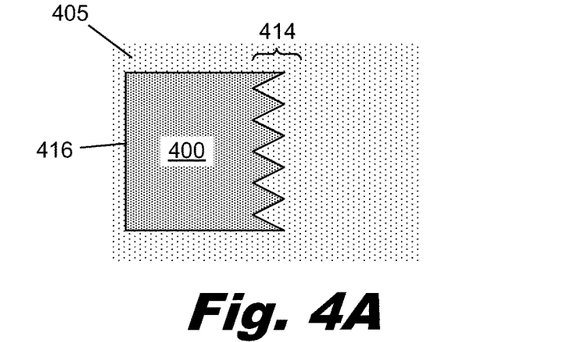
FIG. 4A shows a top view of an electrode with asymmetric edge lengths, according to one example of principles described herein.

FIG. 4A shows an electrode (400) formed on a substrate (405). The electrode (400) has asymmetric edge lengths. The overall shape of the electrode (400) is square, but one side of the electrode has a toothed edge (414). The toothed edge (414) significantly increases the edge length of this portion of the electrode. For example, the three straight edges (416) of the electrode may have lengths of approximately 5 units while the toothed side has an edge length of 10 units. The asymmetric design of this electrode (400) tends to bias the flow of electrical current toward the right toothed edge (414). This preferential current flow can be used to focus the electrical current/field in a desired area or direction. For example, tissues on the left of the electrode will tend to receive less stimulation than tissues on the right of the electrode.

Figure 4B:
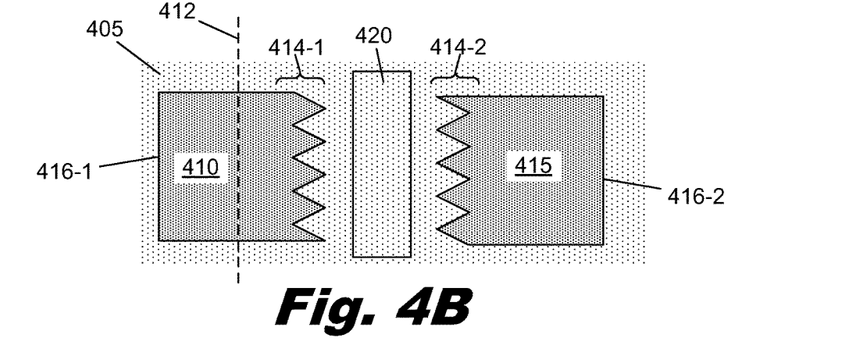
FIG. 4B is a top view of a pair of electrodes with asymmetric edge lengths, according to one example of principles described herein.

FIG. 4B shows a pair of independently driven electrodes (410, 415) that are exposed on the surface of the substrate (405). The left electrode (410) has a generally square shape with a toothed right edge (414-1). The right electrode (415) has a generally square shape with a toothed left edge (414-2). Thus, the toothed edge (414-1) of the left electrode (410) is facing the toothed edge (414-2) of the right electrode (415). As discussed above, tissues that are proximate to the longer length edges will tend to receive greater electrical stimulation. The electrodes (410, 415) may be used together to selectively stimulate the tissue that is between them. For example, a positive voltage could be applied to the left electrode (410) and a negative voltage could be applied to the right electrode (415). This creates an electrical current/field between the two electrodes that is concentrated between the right edge (414-1) of the left electrode and the left edge (414-2) of the right electrode.

The term "asymmetric" refers to the spatial arrangement of the edges or features of the electrode(s). According to one definition, this spatial arrangement lacks symmetry about a central line. The central line may be defined with respect to other electrodes adjacent to the electrode in question or using other reference elements. For example, if the electrode in question is part of a linear array of electrodes, the central line may be perpendicular to the linear array of electrodes and in the same plane as the electrodes. This is illustrated in FIG. 4B by the dashed central line (412) passing through the left electrode (410). This electrode is asymmetrical because the electrode has features on the right of the central line that do not exist on the left side of the line. Split electrodes, such as those in FIGS. 5A and 5B that have asymmetric subparts, may also be called asymmetric electrodes because of the asymmetry within the subparts.

Figure 4C:
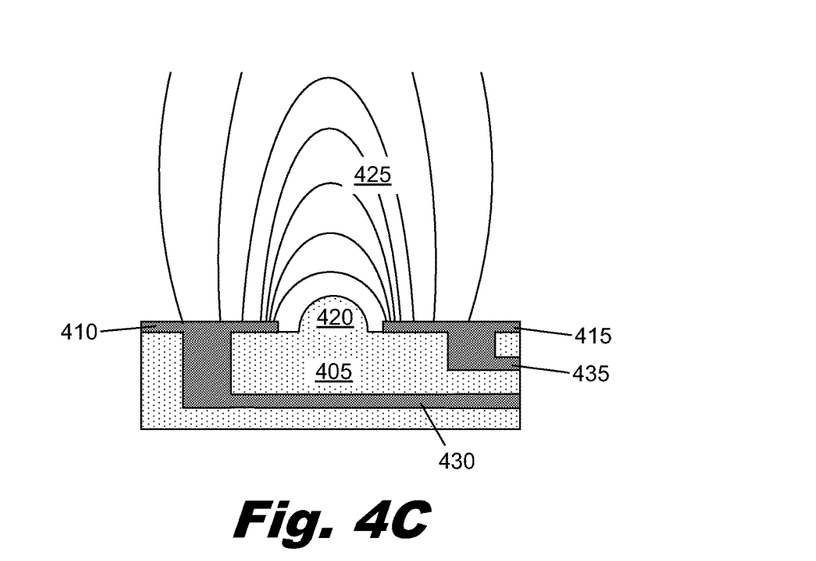
FIG. 4C is a cross sectional diagram of a pair of electrodes with asymmetric edge lengths, according to one example of principles described herein.

A cross sectional diagram of the structure in FIG. 4B is shown in FIG. 4C. As discussed above, the left electrode (410) and right electrode (415) are formed on an insulating substrate (405). The electrodes (410, 415) are connected to electrical traces (430, 435) that allow the electrodes (410, 415) to be independently driven. FIG. 4C shows an illustration of an electrical field (425) generated between the electrodes (410, 415) when they are used as a pair. The illustration of the electrical field (425) shows that electrical field lines tend to be concentrated at the toothed edges (414, FIG. 4B) and that the electrical field (425) is most intense in the region between the toothed edges (414, FIG. 4B). The stimulation presented to the target tissue by the pair of asymmetric electrodes can be a pulsing electrical signal (a direct current signal with varying amplitude) or an electrical signal that alternates polarities (an alternating current signal) with a range of frequencies. The frequencies and amplitudes of the electrical signals can be adjusted for optimum stimulation of the target tissue.

Thus, FIGS. 4B and 4C show a first asymmetric electrode (410) formed on the insulating substrate (405) that has external perimeter edges that include a smooth edge (416-1) with a low edge length and a patterned edge (414-1) with a long edge length. A second asymmetric electrode (415) is formed on the insulating substrate adjacent to the first electrode. The second electrode (415) also includes a smooth edge (416-2) with a low edge length and a patterned edge (414-2) with a long edge length. The patterned edge (414-2) of the second electrode (415) is directly adjacent to the patterned edge (414-1) of the first electrode (410), such that voltages applied to the first electrode (410) and the second electrode (415) generate a concentrated electrical field (425) between the adjacent patterned edges.

Although the examples in FIGS. 4B and 4C show the electrode pair with adjoining toothed edges, electrodes with asymmetric edge lengths may be used in a variety of different configurations. For example, more than two electrodes with asymmetric edge lengths may be used cooperatively to stimulate the desired tissue. In another example, the long edge length sides of the electrodes may not adjoin each other but may be on different sides of the electrodes.

In the example shown in FIGS. 4B and 4C, a protrusion (420) has been formed between the electrodes (410, 415). The protrusion (420) may serve a number of purposes, including protecting the electrodes (410, 415) from abrasion and directing the electrical field (425) into the surrounding tissues. If the protrusion (420) was absent, the strongest electrical field (425) would tend to be along the surface of the substrate that is directly between the toothed edges. This area may not include the desired target tissue.

Figure 5A:
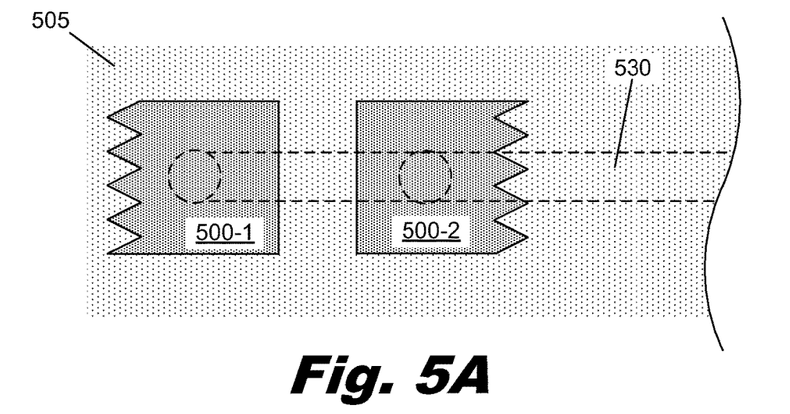
FIGS. 5A-5E are examples of electrodes with long edge length, according to one example of principles described herein.

FIGS. 5A-5E show a variety of electrodes with long edge lengths. FIG. 5A shows an electrode (500) that has been divided into multiple geometrically separate exposed portions. In this example, the electrode (500) has been divided into a left portion (500-1) and a right portion (500-2). A single trace, wire, or other conductor (530) connects to both the left portion (500-1) and the right portion (500-2). The electrode (500) and trace (530) are formed on/in a substrate (505). Each portion of the electrode (500) is asymmetric and has a patterned edge and a smooth edge. A single electrode that is split into multiple sections can provide longer edge lengths and versatility in designing the electrode to selectively stimulate the surrounding tissues.

Figure 5B:
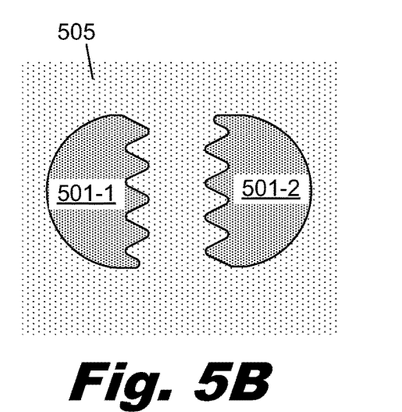

FIG. 5B shows a split electrode (501) formed on a substrate (505) that has a rounded geometry. Again, each portion of the split electrode (501) is asymmetric. The rounded geometry minimizes the edge length of some portions of the electrode (501) to accentuate the current flow through the edges with long lengths. The toothed edges in this example are also rounded to avoid sharp discontinuities along the edge. This may prevent extreme current densities that may occur at sharp tips. When current densities/electrical gradients reach high levels the electricity may alter/damage the biological tissues in close proximity. For example, above a certain threshold the electrolysis of solutions and tissues containing water may occur. This and other chemical changes induced by the electrodes are typically undesirable for nerve or tissue stimulation designs but may be desirable for ablation applications. For example, in a cochlear implant system, damage to the surrounding tissues is typically undesirable. However, if the electrode array is becoming encapsulated in fibrous tissue that increases the impedance between the electrodes and the target tissue, it may be desirable to use higher energy techniques to mitigate the encapsulation in the fibrous tissue.

Figure 5C:
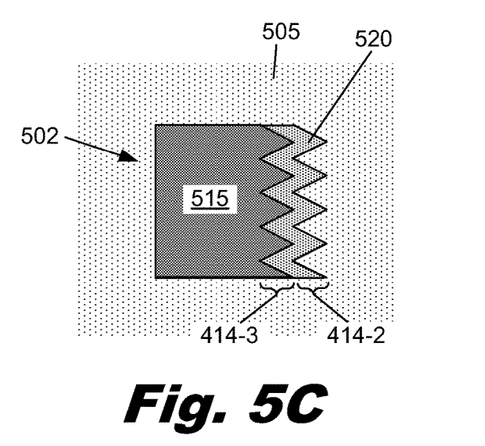

FIG. 5C shows an asymmetric electrode (502) that includes a base (520) that has been cut into a generally square shape with the right edge having a number of teeth that significantly increase the edge length of the right edge. An overcoat (515) has been disposed over the top of the base (520). This overcoat (515) may be shaped into any of a variety of geometries with a variety of edge lengths and edge length-to-surface area ratios. The overcoat (515) may have significantly different characteristics than the base (520). For example, the base (520) may be a relatively smooth platinum electrode. The overcoat (515) may include a dealloyed surface, texturing of the base (520), and/or additional material deposited over the base (520). Dealloyed surfaces for electrodes are further described in U.S. Patent Provisional Application No. 61/582,991, entitled "Porous Dealloyed Bioelectrodes" to Atoosa Lotfi, filed Jan. 4, 2012, which is incorporated herein by reference in its entirety.

Examples of different conductive material that can be deposited over the base include a thin film such as sputtered iridium oxide, titanium nitride, ruthenium oxide, porous niobium oxide, or activated carbon. Other examples of structures which increase the surface area of the electrode include depositing or forming platinum grey, platinum black, sintered platinum, platinum sponges, nanostructures, or other appropriate structures which have high surface areas on the electrode. Platinum gray refers to a platinum microstructure which has a significantly larger surface area than smooth platinum and forms a relatively strong and adhesive film. Platinum black is a fine platinum powder which can be deposited over a solid platinum substrate. This process produces a surface area which is much greater than the geometric surface area of the underlying substrate and exhibits charge transfer characteristics that are superior to non-textured platinum surfaces.

Iridium oxide particles or films could also be used. Iridium oxide films have charge transfer characteristics that are superior to most forms of platinum. Iridium oxide nanoparticles could be joined to form a high surface area layer over the electrode base. The use of a wide variety of additional materials and layers over a base surface are described in U.S. Patent Provisional Application No. 61,288, 201, entitled "Cochlear Electrode Array" to Timothy Beerling et al., filed on Dec. 18, 2009, which is incorporated herein by reference in its entirety. By patterning the base of the electrode with a different material, another "edge" (414-3) can be created at the transition. This edge (414-3) is a boundary between two materials with different electrical characteristics. In some situations, this edge (414-3) may also exhibit some amount of increase in current densities. The edge (414-3) may be formed in a variety of shapes and lengths. The edge (414-3) may further reduce the impedance at the electrode/tissue interface.

Figure 5D:
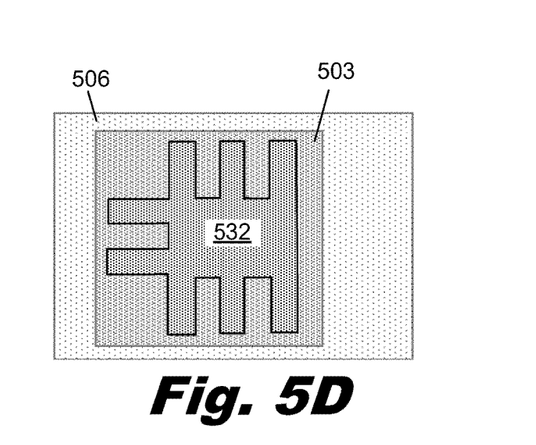

FIG. 5D shows an alternative technique for creating an asymmetric long edge length electrode. In this example, a square conductive structure (503) has been overmolded with an insulating overcoat (506). For example, a platinum electrode may be overmolded with silicone. Portions of the insulating overcoat (506) may then be selectively removed from over the conductive structure (503) so that the exposed portion (532) of the conductive structure forms an asymmetric electrode with a long edge length. The removal of the insulating overcoat (506) may be accomplished using a number of techniques, including laser ablation. The exposed portion (532) of the electrode (503) also has a smaller surface area than the total surface area of an upper surface of the underlying conductive structure.

Figure 5E:
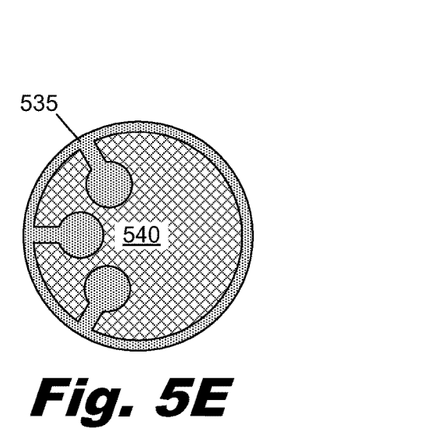

FIG. 5E shows a circular electrode (535) with an asymmetric textured area (540) created on its surface. The asymmetric textured area (540) may have a significantly longer edge length than the external perimeter edge length of the untextured surface of the electrode (535). The textured area (540) may serve a variety of purposes, including increasing the active surface area of the electrode (535), decreasing the adhesion of fibrous tissue to the electrode surface and creating interior edges that decrease the impedance of the electrode (535). The textured area (540) may be formed using a variety of techniques, including depositing additional material or structuring the surface of the electrode. For example, the textured area (540) may be formed by altering the surface texture of the electrode using an excimer laser. The use of an excimer laser to alter the surface texture of an electrode is discussed in Internationalk App. No. PCT/US2013/055102, entitled "Surface Modified Electrodes," filed Aug. 15, 2013, which published as International Pat. Pub. No. WO2015023280 on Feb. 19, 2015, which is incorporated by reference in its entirety. The texturing of the electrode surface can also be used to selectively direct electrical fields to target tissues by changing current densities over the exposed electrode surfaces.

In some examples, texturing the exposed surface of the electrode, or depositing additional material over the exposed surface of the electrode, may result in a first portion of the exposed surface having a lower active surface area-to-geometric surface area ratio and a second portion of the exposed surface with a higher active surface area-to-geometric surface area ratio. For example, for a perfectly smooth surface that is 1 millimeter square, the active surface area will also be 1 millimeter square, resulting in an active surface area-to-geometric surface area ratio of 1:1. However, laser texturing can roughen the surface of the geometric 1 millimeter square portion of the electrode so that its active surface area is 5 square millimeters. This results in an active surface area-to-geometric surface area ratio of 5:1. Similarly, depositing or forming more porous material on the surface can result in a significant increase in the active surface area-to-geometric surface area ratio.

Figure 6:
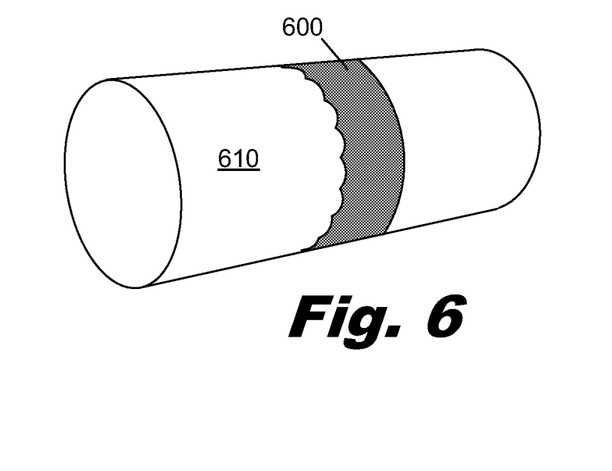
FIG. 6 is a diagram of a ring electrode with long edge length according to one example of principles described herein.

The embodiments described and illustrated above are only examples. A variety of different geometries and materials could be used to implement the principles described herein. For example, FIGS. 5A, 5C and FIG. 5D show the use of electrodes with rectangular or square shapes. The electrodes could have any of a number of shapes, such as round, elliptical, or irregular shapes. For example, FIG. 6 shows a ring electrode (600) that has been formed around a cylindrical body (610). The one edge of the ring electrode (600) has been scalloped to increase its edge length. This may decrease the impedance of the ring electrode.

Figure 7:
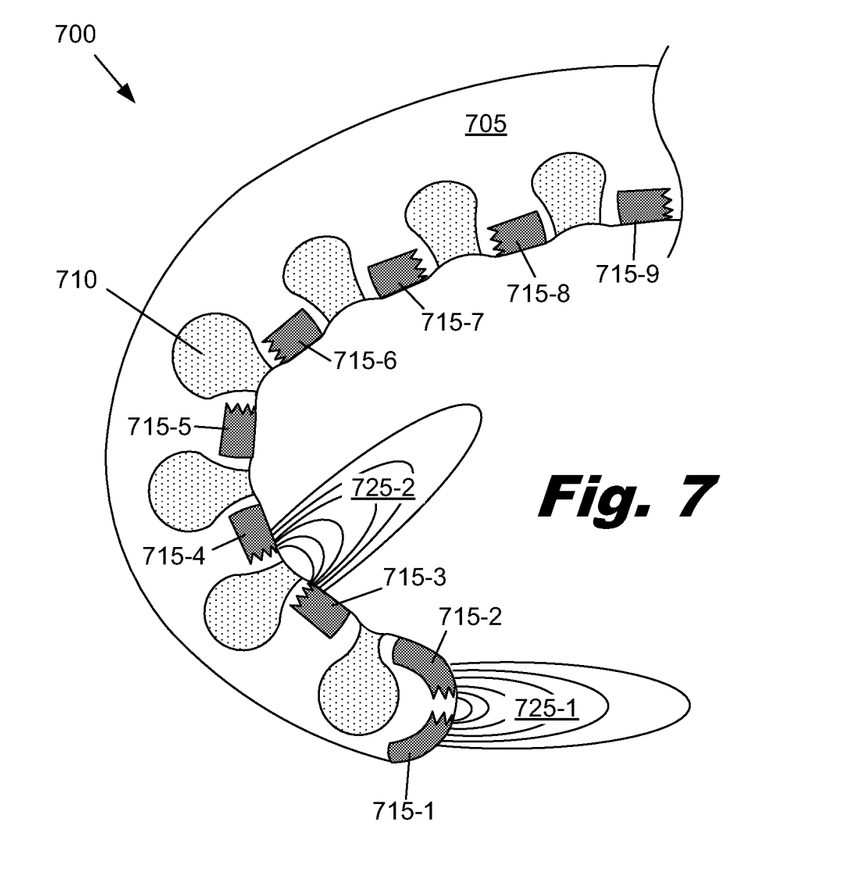
FIG. 7 is a diagram of an implantable lead that includes asymmetric electrodes with long edge length, according to one example of principles described herein.

FIG. 7 shows one example of a cochlear electrode array (700) that includes a number of paired asymmetric electrodes (715) in a linear array. These paired asymmetric electrodes (715) can be used to more selectively stimulate auditory nerves within the cochlea. In one implementation, the electrodes (715) are formed on a circuit substrate (705) that is then cut and thermoformed into the desired shape. The cochlear electrode array (700) may also include a flexible polymer (710) such as silicone. Examples of cochlear electrode arrays that are formed on a thermoformed substrate are given in International App. No. PCT/US2013/056875, "Thermoformed Electrode Arrays," filed on Aug. 27, 2013, which published as International Pat. Pub. No. WO2015030734 on Mar. 5, 2015, which is incorporated herein by reference in its entirety.

In FIG. 7, the electrode pairs are adjacent to each other. For example, electrodes 715-4 and 715-3 are paired. These electrodes have long edge lengths on their adjacent edges. This tends to concentrate the electrical field (725-2) in between the two directly adjacent patterned edges. The shape and intensity of the electrical field (725-2) can be influenced by a variety of factors, including the level of the applied voltage, the material surrounding the electrode array (700), the frequency of the applied voltage, the geometry and material of the electrodes, and other factors. Consequently, the illustrations of electrical fields used herein are not intended to be quantitative representations.

This example also includes a pair of tip electrodes (715-1, 715-2) that are formed on the apical tip of the electrode array. These tip electrodes produce an electrical field (725-1) that extends beyond the tip of the electrode array. These tip electrodes can be used to stimulate lower frequency nerves in the tonotopic arrangement of the cochlea without necessitating deeper insertion of the electrode array into the cochlea. Other electrodes in the linear array of asymmetric electrodes may also be paired together.

The electrode array (700) may be operated to selectively simulate specific groups of auditory nerves. This may be done by selecting adjoining pairs of asymmetric electrodes having adjacent patterned edges and applying a voltage across the asymmetric electrodes. One electrode may have a negative portion of the voltage applied and the other electrode may have a positive portion of the voltage applied. In other examples, one electrode may act as a ground and the other electrode may provide the simulation. Features shown and/or described in connection with one figure may be combined with features shown and/or described in connection with other figures. For example, the cochlear electrode array (700) may include a variety of different electrode types, including the ring electrode (600, FIG. 6) and the electrodes shown and described with respect to FIGS. 3A, 3B, 3C, 5A, 5B, 5C, 5D, and 5E. In some implementations, the electrodes may be configured to be paired with electrodes that are not adjacent in the electrode array. This nonadjacent pairing of electrodes can allow a wider range of targeted tissue to be selectively addressed. The pairings between the electrodes may change as a function of time and may include more than two electrodes. The electrode shapes may be adjusted to have longer edge lengths at specific locations that will allow for the pairings that the electrode will participate in to be used more effectively.

The high edge length electrodes described above could be used in a variety of applications. The use of the electrodes in conjunction with a cochlear implant system is only one example. The high edge length electrodes could be used in biological or other environments. Biological applications could include spinal stimulation, brain stimulation, ocular prosthesis, muscle stimulation, or other applications. The high edge length electrodes could also be used in sensor applications. High edge length electrodes can be effective in reducing the impedance of the interface between the electrodes and the biological tissue, resulting in a more efficient delivery of electrical stimulation and longer battery life.

Where the electrodes are geometrically asymmetric, the electrical behavior of the electrodes may also be asymmetric, with a stronger electrical fields being produced on one side of the electrode than another side. The use of asymmetric electrodes can be used to focus the electrical stimulation on target tissue while minimizing the field in non-target tissue.

The preceding description has been presented only to illustrate and describe examples of the principles described. This description is not intended to be exhaustive or to limit these principles to any precise form disclosed. Many modifications and variations are possible in light of the above teaching.

What is claimed is:

1. An implantable cochlear lead comprising:
    an insulating carrier adapted for placement in a cochlea; and
    first and second stimulation electrodes, each electrode carried by the insulating carrier and bounded by external perimeter edges comprising a jagged edge having an edge length and a smooth edge opposite the jagged edge and having an edge length shorter than the edge length of the jagged edge;
    wherein the jagged edge of the second electrode is disposed facing the jagged edge of the first electrode, and the smooth edge of the second electrode is disposed away from the smooth edge of the first electrode.

2. The lead of claim 1, wherein the first and second stimulation electrodes are located on an apical tip of the lead such that the jagged edge of the first electrode is distal of the smooth edge of the first electrode and the jagged edge of the second electrode is distal of the smooth edge of the second electrode.

3. The lead of claim 1, further comprising:
    third and fourth stimulation electrodes, each electrode carried by the insulating carrier and bounded by external perimeter edges comprising a jagged edge and a smooth edge;
    wherein the smooth edge of the third electrode is disposed adjacent the smooth edge of the second electrode, the jagged edge of the fourth electrode is disposed adjacent the jagged edge of the third electrode, and the smooth edge of the fourth electrode is disposed away from the smooth edge of the third electrode.

4. The lead of claim 1, wherein the first stimulation electrode has an overall shape that is rectangular or round.

5. The lead of claim 1, wherein the first stimulation electrode is a ring.

6. The lead of claim 1, wherein the jagged edges are toothed, slotted, castellated, or scalloped.

7. The lead of claim 6, wherein the jagged edges have regular teeth, slots, castellations, or scallops.

8. The lead of claim 1, wherein the insulating carrier comprises a thermoformed substrate.

9. The lead of claim 8, further comprising a pocket of flexible polymer formed in the substrate between the first and second electrodes, wherein the flexible polymer has a greater flexibility than the substrate.

10. The lead of claim 1, further comprising a protrusion between the jagged edges, the protrusion configured to direct an electrical field into target tissue.

11. A method for stimulating target tissue comprising:
    implanting the lead of claim 1 in a cochlea; and
    applying a voltage across the first and second stimulation electrodes to stimulate the target tissue.

12. A method for stimulating target tissue comprising:
    implanting the lead of claim 1 in a cochlea;
    electrically coupling the first stimulation electrode to the second stimulation electrode to form a split electrode; and
    applying a voltage across the split electrode and one or more other electrodes that are not adjacent the first or second stimulation electrodes to stimulate the target tissue.

13. An implantable cochlear lead comprising:
    an insulating carrier adapted for placement in a cochlea;
    a first stimulation electrode carried by the insulating carrier and bounded by external perimeter edges comprising:
        a jagged edge having an edge length, and
        a smooth edge opposite the jagged edge and having an edge length shorter than the edge length of the jagged edge; and
    a second stimulation electrode carried by the insulating carrier and bounded by external perimeter edges comprising:
        a jagged edge having an edge length, and
        a smooth edge opposite the jagged edge and having an edge length shorter than the edge length of the jagged edge;
    wherein the first and second electrodes are disposed on a distal tip of the lead with their jagged edges facing each other and distal of their smooth edges.

14. The lead of claim 13, wherein the first stimulation electrode has an overall shape that is rectangular.

15. The lead of claim 13, wherein the first stimulation electrode has an overall shape that is round.

16. The lead of claim 13, wherein the jagged edges are toothed, slotted, castellated, or scalloped.

17. The lead of claim 16, wherein the jagged edges are serpentine or have rounded peaks.

18. The lead of claim 16, wherein the jagged edges have regular teeth, slots, castellations, or scallops.

19. A method for stimulating target tissue comprising:
    implanting the lead of claim 13 in a cochlea; and applying a voltage across the first and second stimulation electrodes to stimulate the target tissue.

20. A method for stimulating target tissue comprising:
implanting the lead of claim 13 in a cochlea;
electrically coupling the first stimulation electrode to the second stimulation electrode to form a split electrode; and
applying a voltage across the split electrode and one or more other electrodes that are not adjacent the first or second stimulation electrodes to stimulate the target tissue.

* * * * *